(12) United States Patent
Anderson et al.

(10) Patent No.: US 11,607,243 B2
(45) Date of Patent: Mar. 21, 2023

(54) SOFT TISSUE CUTTING INSTRUMENT WITH RETRACTABLE BLADE OR HOOK

(71) Applicant: CONMED CORPORATION, Utica, NY (US)

(72) Inventors: Sharon K. Anderson, St. Petersburg, FL (US); Khiem Pham, Largo, FL (US); James Hutter, Largo, FL (US)

(73) Assignee: CONMED CORPORATION, Utica, NY (US)

( * ) Notice: Subject to any disclaimer, the term of this patent is extended or adjusted under 35 U.S.C. 154(b) by 226 days.

(21) Appl. No.: 16/621,825

(22) PCT Filed: Jun. 7, 2018

(86) PCT No.: PCT/US2018/036414
§ 371 (c)(1),
(2) Date: Dec. 12, 2019

(87) PCT Pub. No.: WO2018/231617
PCT Pub. Date: Dec. 20, 2018

(65) Prior Publication Data
US 2021/0275206 A1    Sep. 9, 2021

Related U.S. Application Data

(60) Provisional application No. 62/652,365, filed on Apr. 4, 2018, provisional application No. 62/597,612, filed
(Continued)

(51) Int. Cl.
*A61B 17/3211* (2006.01)
*A61B 90/00* (2016.01)
*A61B 17/00* (2006.01)

(52) U.S. Cl.
CPC .......... *A61B 17/3211* (2013.01); *A61B 90/03* (2016.02); *A61B 90/08* (2016.02);
(Continued)

(58) Field of Classification Search
CPC . A61B 17/3209; A61B 17/3211; A61B 17/34; A61B 2017/32113; A61B 90/03; A61B 2090/0801; A61B 17/320036
See application file for complete search history.

(56) References Cited

U.S. PATENT DOCUMENTS 2,623,521 A * 12/1952 Shaw ..................... A61M 5/32
                                              604/170.02
5,172,701 A * 12/1992 Leigh ................. A61B 10/0283
                                              600/566
(Continued)

FOREIGN PATENT DOCUMENTS

JP        2003504109 A     2/2003
JP        2006524113       10/2006
(Continued)

OTHER PUBLICATIONS

JP Office Action, App. No. 2019-568244, pp. 1-6, dated May 11, 2021.
(Continued)

*Primary Examiner* — Ryan J. Severson
(74) *Attorney, Agent, or Firm* — Bond, Schoeneck & King, PLLC; Frederick J. M. Price

(57) ABSTRACT

A system and method for cutting soft tissue with a retractable surgical cutting device (10). The device (10) includes a handle (12) having a first channel (24) extending therethrough and a switch (18) located thereon. The switch (18) is movable between a retracted position and an extended position. An actuator (26) with a blade (16) extends through the first channel (24) and connects to the switch (18) within the handle (12). An outer sheath (14) is connected to the handle (12) and surrounds the actuator (26) and at least a portion of the blade (16). A drive mechanism (28) is connected to the switch (18) within the handle (12) such that when the switch (18) moves from the retracted position to
(Continued)

the extended position, the actuator (26) moves from a retracted position to an extended position. In the retracted position, the blade (16) can be entirely within the outer sheath (14) and in the extended position, at least a portion of the blade (16) is positioned outside of the outer sheath (14).

10 Claims, 20 Drawing Sheets

Related U.S. Application Data on Dec. 12, 2017, provisional application No. 62/524,769, filed on Jun. 26, 2017, provisional application No. 62/518,803, filed on Jun. 13, 2017.

(52) U.S. Cl.
CPC .............. *A61B 2017/00367* (2013.01); *A61B 2017/32113* (2013.01); *A61B 2090/034* (2016.02); *A61B 2090/0801* (2016.02)

(56) References Cited

U.S. PATENT DOCUMENTS

| | | | |
|---|---|---|---|
| 5,201,741 A * | 4/1993 | Dulebohn | A61B 17/32056 606/113 |
| 5,207,696 A | 5/1993 | Matwijcow | |
| 5,904,699 A | 5/1999 | Schwemberger et al. | |
| 6,623,499 B1 | 9/2003 | Andreini et al. | |
| 6,749,576 B2 * | 6/2004 | Bauer | A61B 10/0275 600/564 |
| 7,159,713 B1 | 1/2007 | Austria | |
| 7,387,637 B2 | 6/2008 | Morawski et al. | |
| 8,202,277 B2 * | 6/2012 | Ryan | A61F 9/007 606/107 |
| 8,308,737 B2 * | 11/2012 | Ryan | A61F 9/007 606/107 |
| 9,872,701 B2 * | 1/2018 | Werner | A61B 17/3211 |
| 9,918,801 B2 | 3/2018 | Takei | |
| 9,931,244 B2 * | 4/2018 | Ryan | A61F 9/00736 |
| 10,022,110 B2 | 7/2018 | Stand, III et al. | |
| 10,123,815 B2 | 11/2018 | Huffenus et al. | |
| 10,898,373 B2 * | 1/2021 | Ryan | A61F 9/00736 |
| 2002/0002376 A1 * | 1/2002 | Gannoe | A61B 17/3496 606/167 |
| 2003/0032969 A1 * | 2/2003 | Gannoe | A61B 17/320016 606/167 |
| 2004/0186484 A1 * | 9/2004 | Ryan | A61F 9/007 606/107 |
| 2005/0033336 A1 | 2/2005 | Chang-Ming | |
| 2006/0241664 A1 | 10/2006 | Lam | |
| 2009/0192538 A1 | 7/2009 | Sandel et al. | |
| 2013/0245655 A1 * | 9/2013 | Mahurkar | A61B 17/3211 606/167 |
| 2015/0216585 A1 | 8/2015 | Kirstgen et al. | |
| 2016/0235430 A1 * | 8/2016 | Huffenus | A61B 17/320016 |
| 2017/0112521 A1 * | 4/2017 | Werner | A61B 17/3211 |

FOREIGN PATENT DOCUMENTS

| | | |
|---|---|---|
| JP | H10508510 A | 1/2008 |
| JP | 2015147044 | 8/2016 |
| WO | 1993/25152 | 12/1993 |
| WO | WO 01/54588 | 8/2001 |
| WO | 2005/033336 | 4/2005 |
| WO | WO 2013/134489 | 9/2013 |
| WO | WO 2016/160581 | 10/2016 |

OTHER PUBLICATIONS

EP Communication 161(1) and 162 EPC, App. No. 19791397.3, pp. 1-2, dated May 14, 2021.
AU Exam Report, App. No. 2019353012, dated Aug. 23, 2021, pp. 1-4.
JP Office Action, App. No. 2021-518163, pp. 1-12, dated Mar. 29, 2022.
CA Office Action, App. No. 3066370, dated Aug. 29, 2022, pp. 1-4.
EU Communication 94(3), App. No. 19791397.3, dated May 19, 2022, pp. 1-6.

\* cited by examiner

SOFT TISSUE CUTTING INSTRUMENT WITH RETRACTABLE BLADE OR HOOK

CROSS-REFERENCE TO RELATED APPLICATION

The present application relates and claims priority to U.S. Provisional Patent Application Ser. Nos. 62/518,803 filed Jun. 13, 2017, 62/524,769 filed Jun. 26, 2017, 62/597,612 filed Dec. 12, 2017 and 62/652,365 filed Apr. 4, 2018.

BACKGROUND OF THE INVENTION

1. Field of the Invention

The invention relates generally to surgical device for cutting soft tissue and more particularly, a soft tissue cutting instrument with a retractable blade or hook

2. Description of Related Art

During surgery, soft tissue is incised by inserting a cutting device with a surgical blade or hook blade into a surgical site within the body. Some current cutting devices have an exposed surgical blade or hook blade. If the blade on the cutting device is exposed, there is a potential of injury to both the user and the patient. In one example, the user is at risk of injury from the exposed blade while handling the cutting device. In another example, the patient is at risk of injury when the exposed blade enters or exits the body. When an exposed blade enters or exits the body, it may inadvertently cut soft tissue.

In addition, current cutting devices are not ergonomically designed for the user, which may also contribute to mishandling and risk injury of the user and the patient.

Therefore, there is a need for an easy-to-use surgical instrument for cutting soft tissue that has a protectable blade or hook blade.

SUMMARY OF THE INVENTION

The present invention is directed to, inter alia, a system and method for cutting tissue with a retractable surgical cutting device. In one embodiment, the present invention is a retractable surgical cutting device. The device includes a handle having a first channel extending therethrough. A switch located on the handle, the switch being movable between a retracted position and an extended position. An actuator extends through the first channel and connects to the switch within the handle. The actuator also comprises a blade at its distal end. The blade can include, but is not limited to, any shaped blade including a straight blade, angled blade (angled from itself and/or the shaft), curved blade (curved from itself and/or the shaft) or a hook blade etc. An outer sheath is connected to the handle and surrounds the actuator and at least a portion of the blade. A drive mechanism is connected to the switch within the handle such that when the switch moves from the retracted position to the extended position, the actuator moves from a retracted position to an extended position. When the actuator is in the retracted position, the blade can be (although does not have to be) entirely within the outer sheath (as in a preferred embodiment), and when the actuator is in the extended position, at least a portion of the blade is out of the outer sheath.

In another embodiment of the device, the device includes a handle having a first channel extending therethrough and a switch located thereon. The switch is movable between a retracted position and an extended position. An actuator extends through the first channel and connects to a proximal end of the first channel within the handle. The actuator has a blade at its distal end. An outer sheath surrounds the actuator and at least a portion of the blade. The outer sheath interfaces with the switch. A drive mechanism is connected to the switch within the handle such that when the switch moves from the retracted position to the extended position, the outer sheath moves from a retracted position to an extended position. When the outer sheath is in the retracted position, the blade is fully positioned within (although does not have to be) the outer sheath (as in a preferred embodiment) and when the outer sheath is in the extended position, at least a portion of the blade is positioned outside of the outer sheath.

In one embodiment, the present invention provides a method for cutting tissue. The method comprises the steps of: (i) providing a retractable surgical cutting device having a handle with a first channel extending therethrough, a switch located on the handle which is movable between a retracted position and an extended position, an actuator which extends to a proximal end of the first channel, a blade at a distal end of the actuator, an outer sheath interfacing the switch, the outer sheath surrounding the actuator and at least a portion of the blade; and a drive mechanism connected to the switch within the handle; (ii) moving the switch in a first direction along a longitudinal x-axis extending through the device; (iii) moving the outer sheath, via the drive mechanism, relative to the actuator; and (iv) exposing at least a portion of the blade. The method can further include the steps of advancing the outer sheath into a surgical site, and cutting tissue at a surgical site with the blade.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
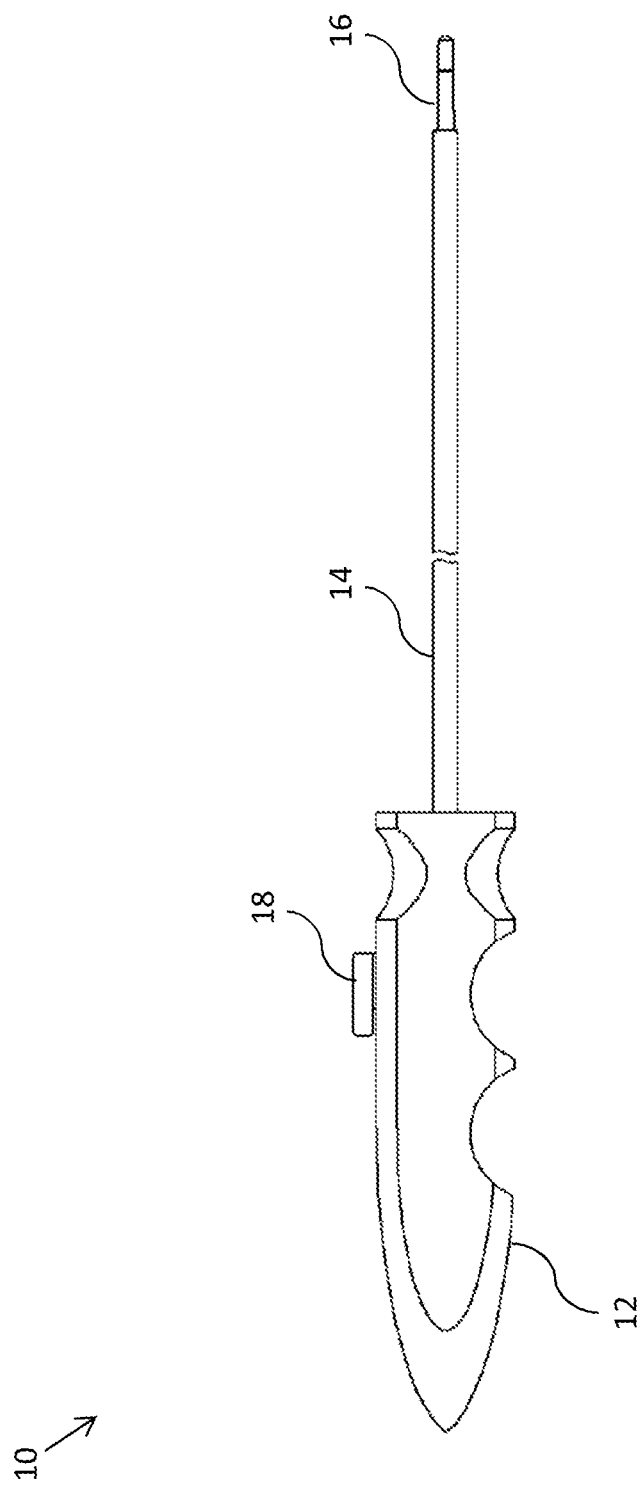
FIG. 1 is a side view schematic representation of an illustrative embodiment of a retractable surgical cutting device.

Referring now to FIG. 1, there is shown a side view schematic representation of an illustrative embodiment of a retractable surgical cutting device 10. The device 10 comprises a handle 12 connected to an outer sheath 14, which extends to a distal blade 16. The blade 16 is selectively extended and retracted upon actuation of a switch (or button) 18 on the handle 12, as will be explained in detail later. As shown in FIG. 1, the handle 12 can include thumb and finger grooves such that the shape of the handle 12 is ergonomic. The ergonomic design of the handle 12 provides increased control of the device 10 for its intended use. In other embodiments, the handle 12 may have fewer grooves or no grooves entirely. In some embodiments, the handle 12 is composed of plastic; however, the handle 12 may be composed of stainless steel or other traditional materials suitable for surgical devices.

Figure 2:
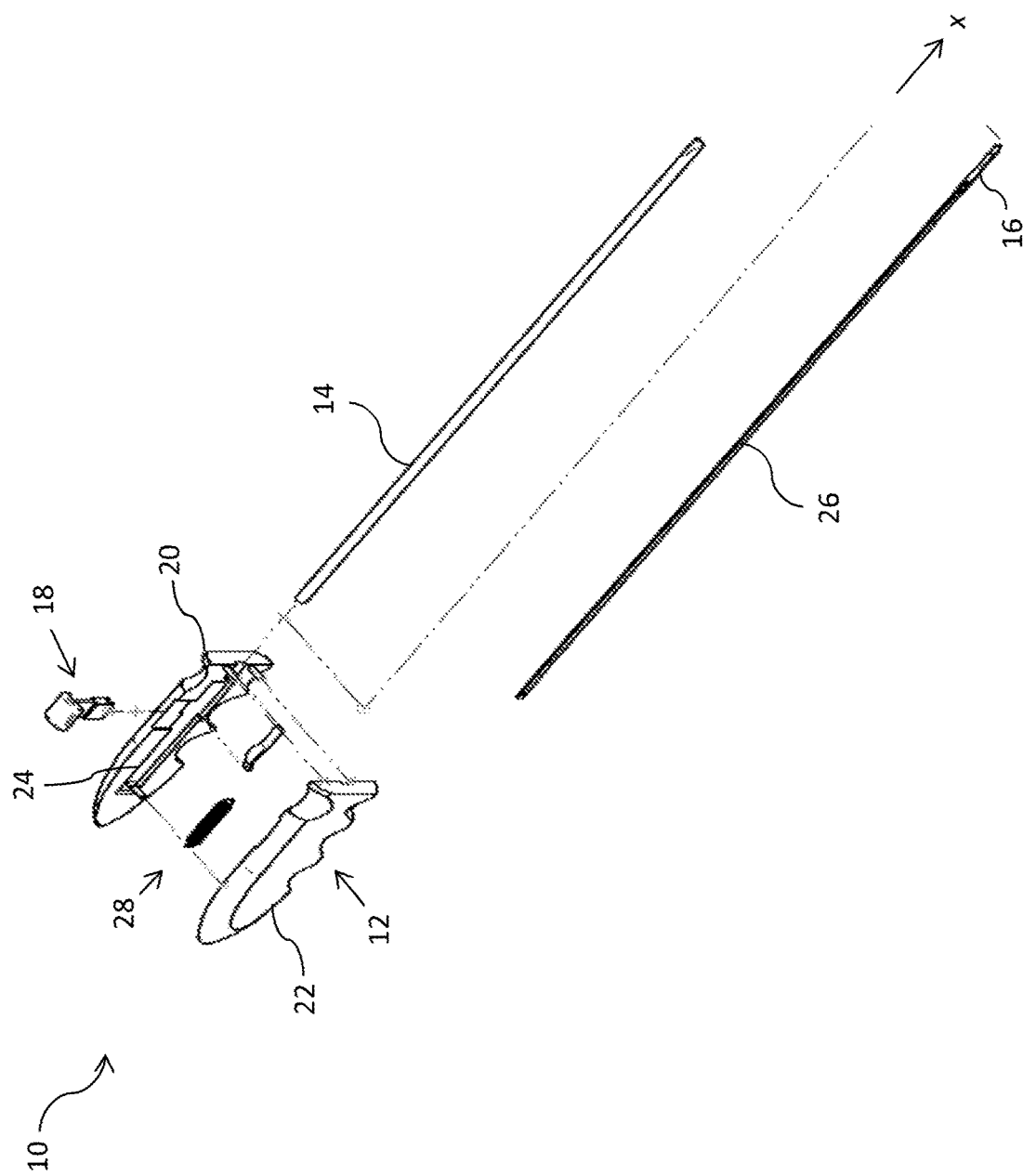
FIG. 2 is an exploded perspective view schematic representation of an illustrative embodiment of the retractable surgical cutting device of FIG. 1.

Turning now to FIG. 2, there is shown an exploded view schematic representation of the illustrative embodiment the retractable surgical cutting device 10 of FIG. 1. In the depicted embodiment, the handle 12 of the device 10 is comprised of two pieces, a first piece 20 and a second piece 22, having one or more channels therethrough. It is contemplated that in an alternative embodiment, the handle 12 may be composed of a single piece molded or otherwise formed around the inner components of the handle 12. Continuing with FIG. 2, the handle 12 comprises a first channel 24, which is sized, dimensioned, and otherwise configured for an actuator 26, which is connected to the blade 16. The actuator 26 moves longitudinally within the outer sheath 14 in both directions along an x-axis, which extends approximately through the center of the handle 12. The longitudinal movement of the actuator 26 is caused by a drive mechanism 28 within the handle 12, as will be described in detail later. In other embodiments, the actuator 26 remains stationary while the drive mechanism 28 moves the outer shaft 14 relative to the actuator 26 and the blade 16. In the one embodiment, the actuator 26 comprises the blade 16 machined on its distal end 30. Thus, the embodiment of the actuator 26 and blade 16 can be a single-piece embodiment.

Figure 3B:
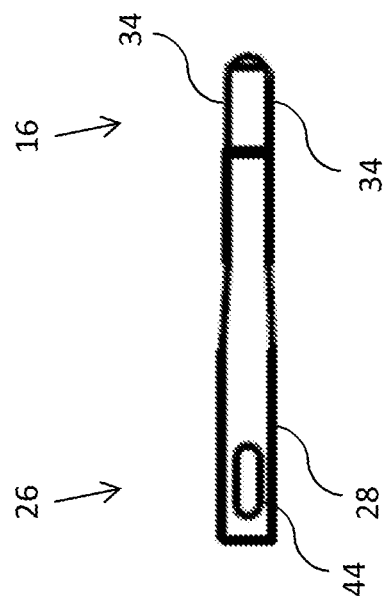
FIG. 3B is a top view schematic representation of an illustrative embodiment of a blade.
Figure 3A:
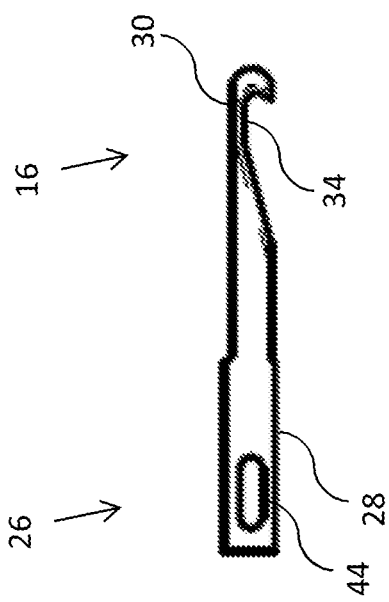
FIG. 3A is a top view schematic representation of an illustrative embodiment of a hook blade.

Referring now to FIGS. 3A-3B, there are shown top view schematic representations of illustrative embodiments of a blade. The blade 16 in FIGS. 3A-3B comprises an aperture 44 for connecting to the actuator 26 in a two-piece embodiment of the actuator 26 and blade 16. FIG. 3A shows an embodiment wherein the blade 16 is a hook blade having at least one sharp edge 34 and one non-sharp edge 30. FIG. 3B shows an embodiment wherein the blade 16 is a surgical blade with two sharp edges 34 (e.g., top and bottom). Any combination and number of sharp edges 34 and/or non-sharp edges 30 is contemplated for the blade 16.

Figure 4:
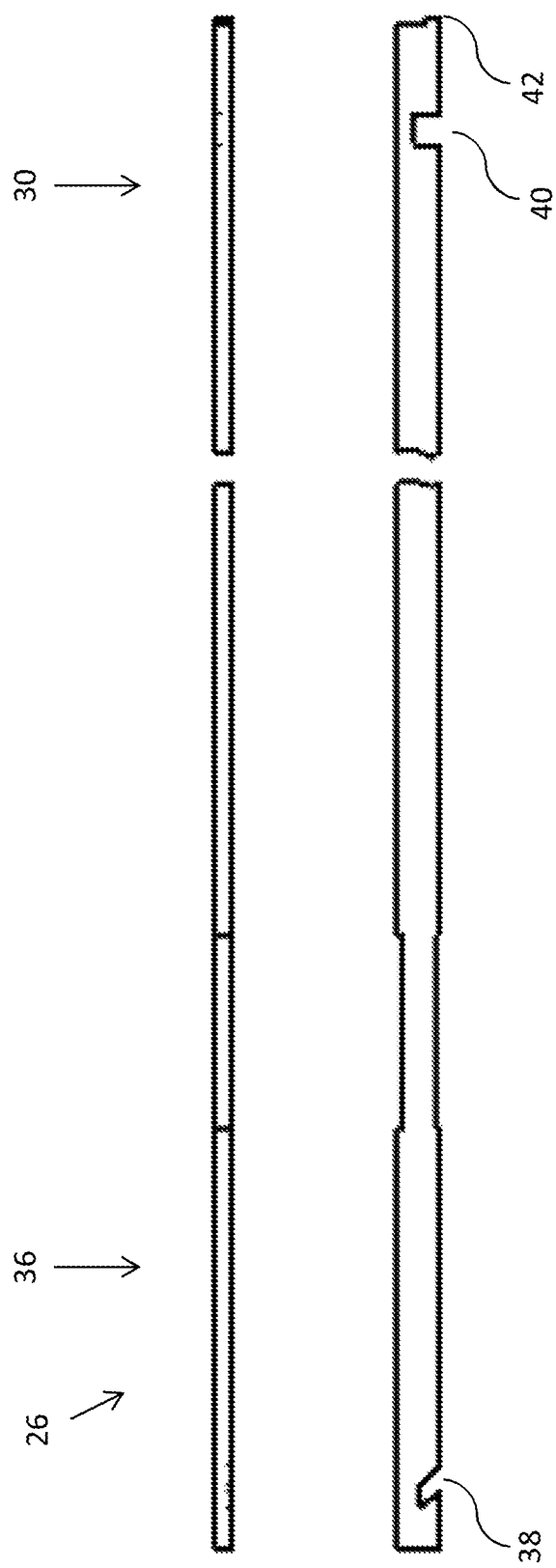
FIG. 4 is a top view and side view schematic representation of an illustrative embodiment of a two-piece actuator.

Referring now to FIG. 4, there is shown a top and side view schematic representation of an illustrative embodiment of the actuator 26 of a two-piece actuator 26 and blade 16. In comparison to a one-piece actuator 26 including the blade 16, the actuator 26 of FIG. 4 is separate from and not otherwise machined onto the blade 16. The actuator 26 in FIG. 4 comprises one or more notches for connecting to the blade 16 and the drive mechanism 28. At the proximal end 36 of the actuator 26 there is a notch 38 for connecting the actuator 26 to the drive mechanism 28. In another embodiment, the notch 38 at the proximal end 36 may be an aperture or other means for attaching the drive mechanism 28 to the actuator 26. The actuator 26 can also comprise one or more notches 40, 42 at its distal end 30. The notches 40, 42 at the distal end 30 of the actuator 26 are configured for attachment to the blade 16.

Figure 5B:
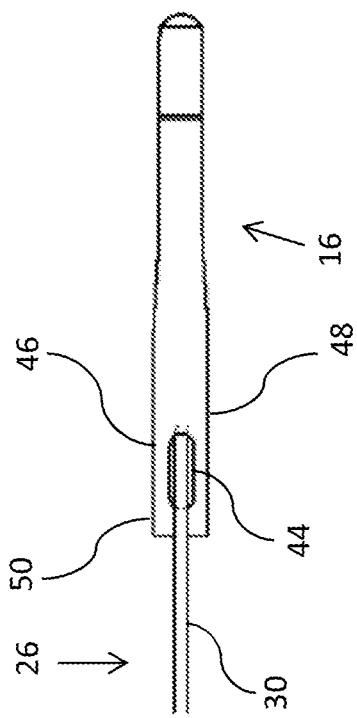
FIG. 5B is a top view schematic representation of an illustrative embodiment of the two-piece actuator of FIG. 4 connected to a blade.
Figure 5A:
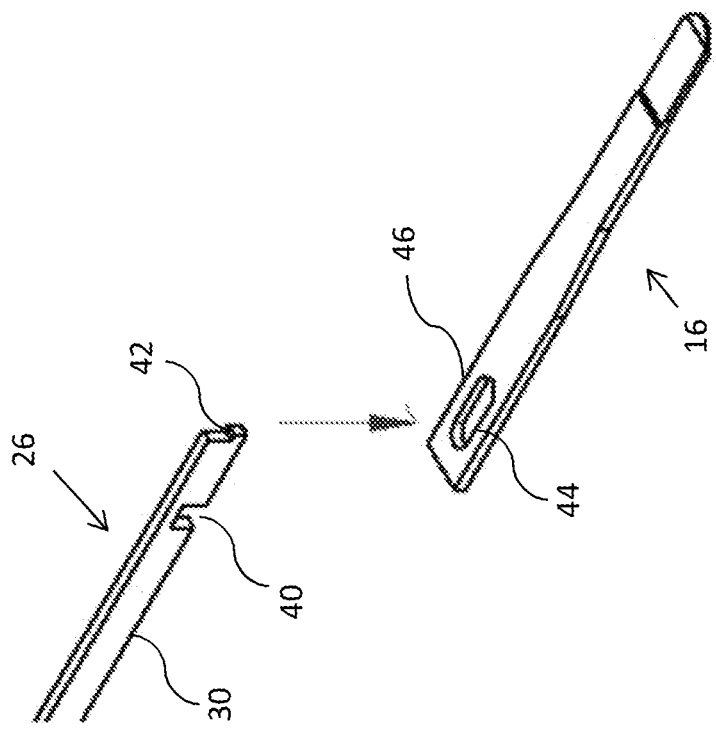
FIG. 5A is a perspective view schematic representation of an illustrative embodiment of the two-piece actuator of FIG. 4 and a blade.
Figure 5D:
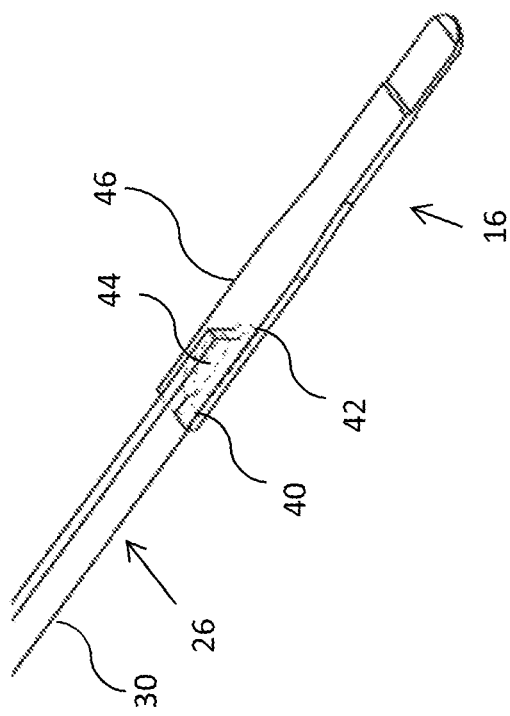
FIG. 5D is a perspective view schematic representation of an illustrative embodiment of the two-piece actuator of FIG. 4 connected to a blade.
Figure 5C:
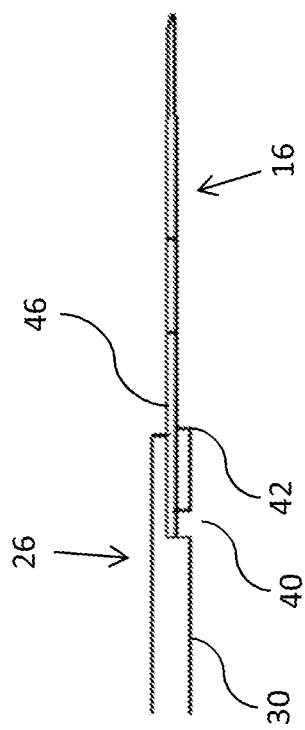
FIG. 5C is a side view schematic representation of an illustrative embodiment of the two-piece actuator of FIG. 4 connected to a blade.

Turning now to FIGS. 5A-5D, there are shown various views of schematic representations of an illustrative embodiment of the distal end 30 of the two-piece actuator 26 and blade 16. As shown in FIG. 5A, the distal end 30 of the actuator 26 has a first notch 40 and a second notch 42, while the blade 16 has an aperture 44 at its proximal end 46. In the depicted embodiment, the first notch 40 and the second notch 42 have recesses which extend in directions opposing each other. To assemble the two-piece actuator 26 and blade 16, the distal end 30 of the actuator 26 is inserted at an angle into the aperture 44 at the proximal end 46 of the blade 16. The distal end 30 of the actuator 26 is so inserted until the second notch 42 is through the aperture 44. Thereafter, the proximal end 36 of the actuator 26 (shown in FIG. 4) is rotated away from the blade 16 and into the same plane as the blade 16, locking the blade 16 into place, as shown in FIGS. 5C-5D. The second notch 42 on the distal end 30 of the actuator 26 engages the blade 16 on a distal side 48 of the aperture 44, while the first notch 40 engages the blade 16 on a proximal side 50 of the aperture 44, as shown in FIG. 5B.

Figure 6:
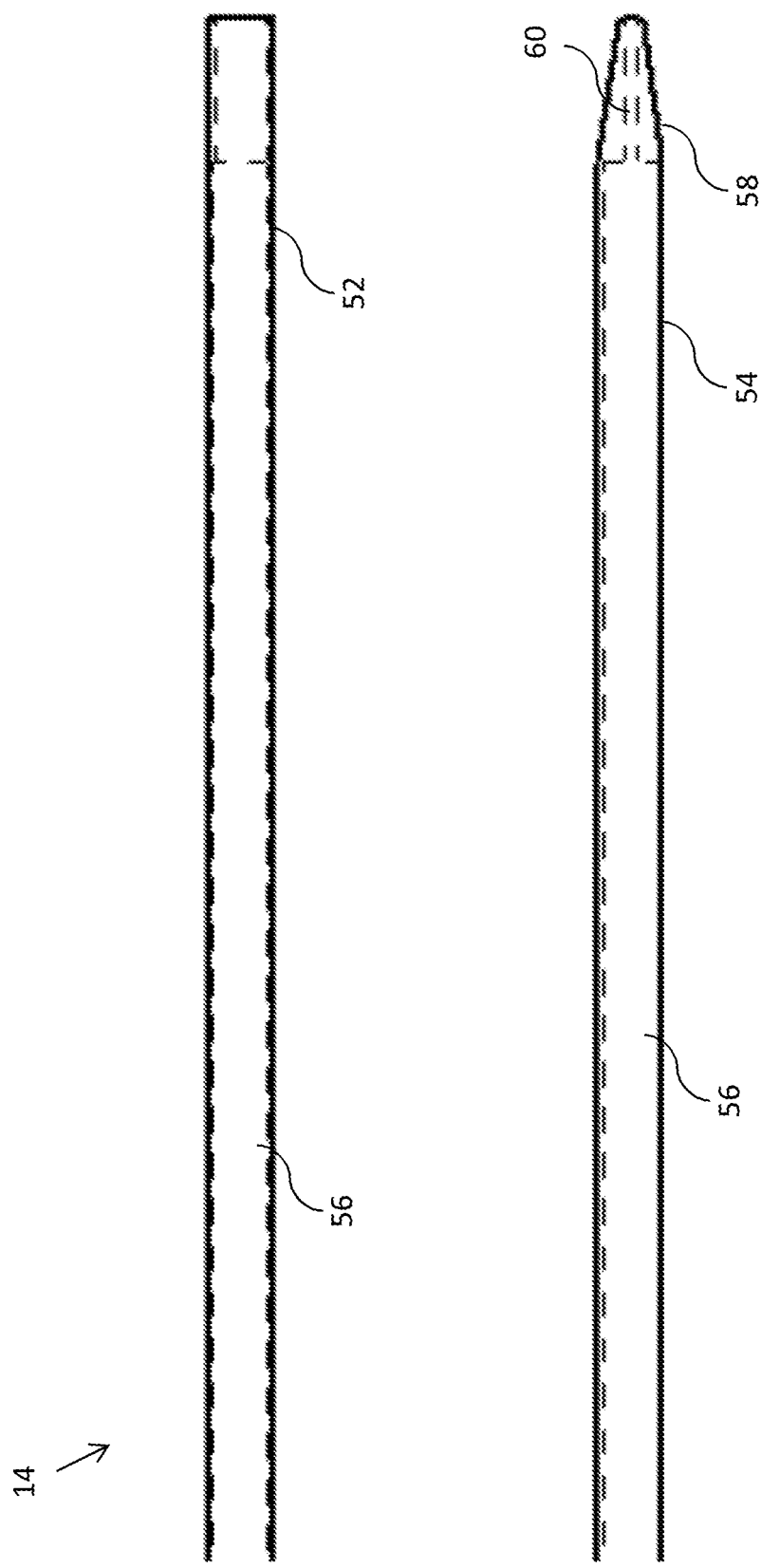
FIG. 6 is a side view schematic representation of an illustrative embodiment of the outer sheath.

Referring now to FIG. 6, there is shown a top view schematic representation of an illustrative embodiment of a proximal end 52 and a distal end 54 of an outer sheath 14. In the depicted embodiment, the outer sheath 14 is cannulated such that the outer sheath 14 has a first inner volume 56. The outer sheath 14 is sized and dimensioned to fit around the actuator 26 and at a least a portion of the blade 16. In other words, the actuator 26 and the blade 16 are inserted into the first inner volume 56 of the outer sheath 14 such that the outer sheath 14 surrounds the actuator 26 and at least a portion of the blade 16 (as shown in FIG. 1). The outer sheath 14 is fixed to the handle 12 of the device 10 such that the longitudinal movement of the actuator 26 (via the drive mechanism 28) extends and retracts the blade 16 from the outer sheath 14. In alternative embodiments, the outer sheath 14 is fixed to the switch 18 and longitudinal movement of the switch along the x-axis moves the outer sheath 14 relative to a stationary actuator 26 and blade 16.

FIG. 6 also shows an embodiment wherein the outer sheath 14 has a narrow portion 58. The narrow portion 58 of the outer sheath 14 has a second inner volume 60 with a diameter smaller than the diameter of the first inner volume 56 of the outer sheath 14. In one embodiment, the narrow portion 58 is tapered in a direction toward the distal end 30 of the actuator 26 and blade 16, as shown in FIG. 6. However, the narrow portion 58 does not need to be tapered in order to have a second inner volume 60 with a diameter smaller than the diameter of the first inner volume 56. The narrow portion 58 having a second inner volume 60 with a smaller diameter aids in preventing the potential of the blade 16 from inadvertently becoming disconnected from the actuator 26 (in the two-piece embodiment). The narrow portion 58 can also provide an a-traumatic tip to prevent damage at or near the surgical site based on its shape and/or being composed of non-metal material, such as PEEK. In the event of a failure of the notches 40, 42 securing the blade 16 to the actuator 26, the narrow portion 58 and the second inner volume 60 maintain the blade 16 within the outer sheath 14 as opposed to falling from the device 10.

Figure 7:
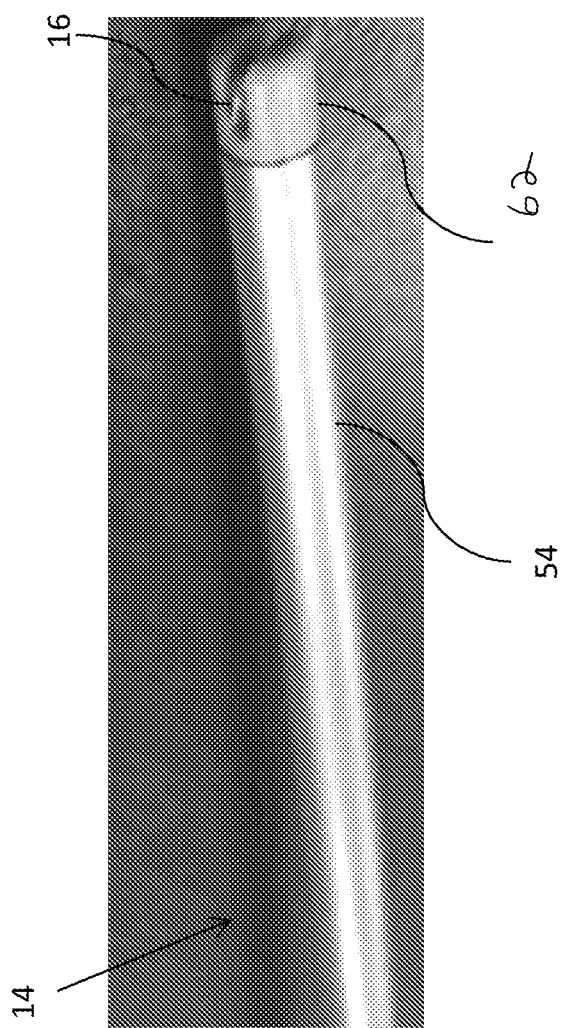
FIG. 7 is a close-up perspective view schematic representation of an alternative illustrative embodiment of the outer sheath.

Turning briefly to FIG. 7, there is shown a close-up perspective view schematic representation of an alternative illustrative embodiment of the distal end 54 of the outer sheath 14. In the depicted embodiment, the distal end 54 does not have a narrow portion 58. The distal end 54 of the outer sheath 14 has an insert 62. The insert 62 is preferably composed of non-metal material, such as PEEK. The insert 62 provides an a-traumatic tip to prevent damage at or near the surgical site. For example, the insert 62 is configured to prevent damage to cartilage structures within a joint space. FIG. 7 shows the blade 16 recessed within the insert 62 to allow for introduction of the outer sheath 14 and the blade 16 into the surgical site (e.g., joint space) either with or without a cannula.

Figure 8A:
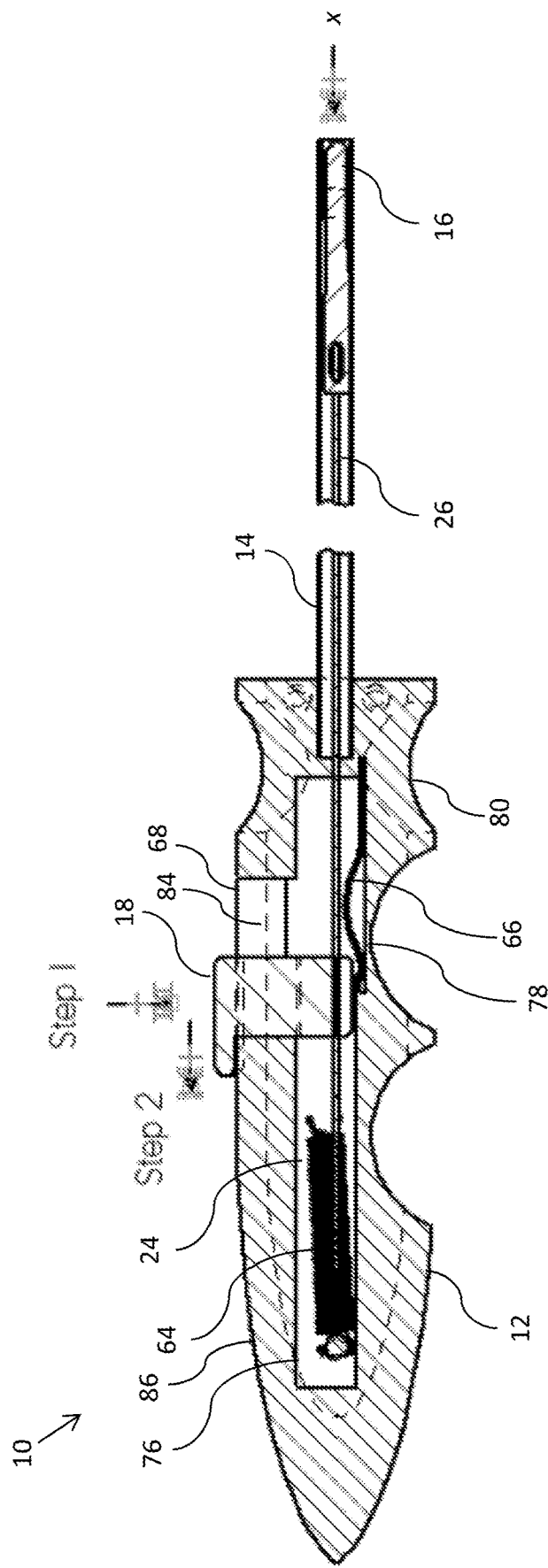
FIG. 8A is a cutaway side view schematic representation of an illustrative embodiment of the retractable surgical cutting device of FIG. 1 in the retracted position.
Figure 8B:
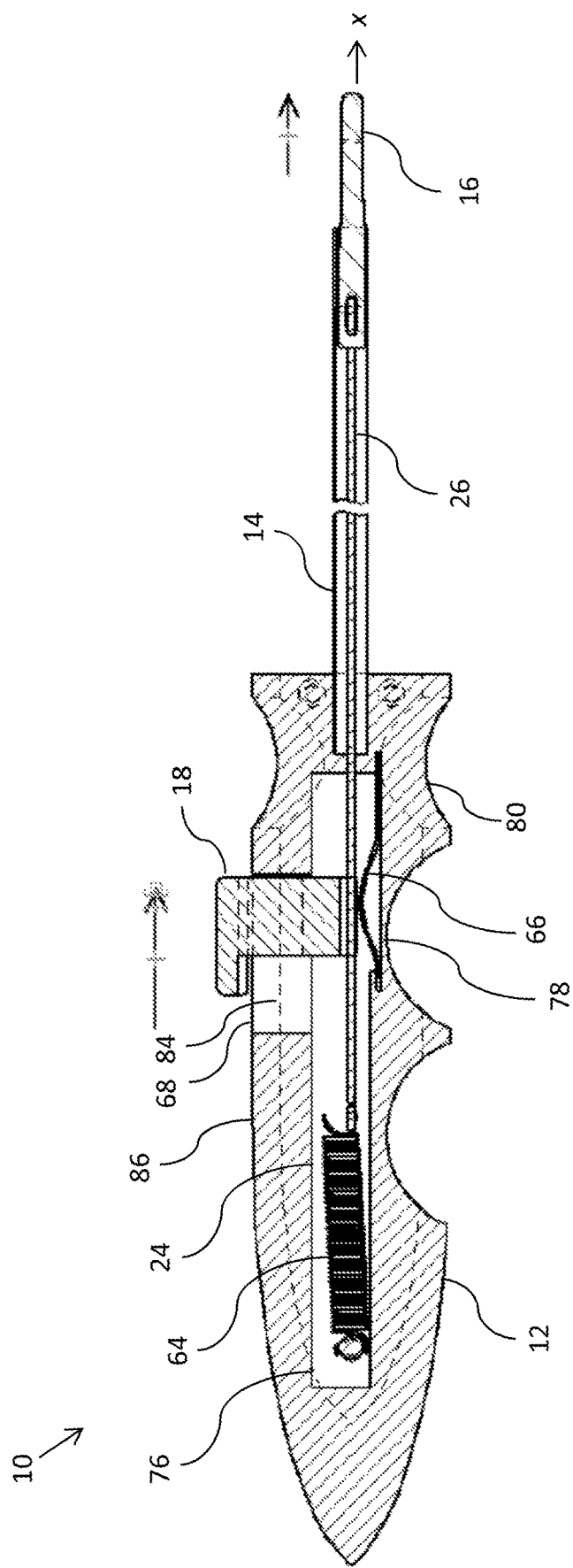
FIG. 8B is a cutaway side view schematic representation of an illustrative embodiment of the retractable surgical cutting device of FIG. 1 in the extended position.

Referring now to FIGS. 8A-8B, there are shown cutaway side view schematic representations of an illustrative embodiment of the retractable surgical cutting device of FIG. 1 in the retracted and extended positions, respectively. The handle 12 comprises a drive mechanism 28 therein, which facilitates movement of the actuator 26 and blade 16 longitudinally in both directions along an x-axis within the outer sheath 14. In the embodiment shown in FIGS. 8A-8B, the drive mechanism 28 comprises a pair of springs. The pair of springs includes an extension spring 64 and a flat spring 66 (or thin metal piece). In the depicted embodiment, the extension spring 64 is a coil spring and the flat spring 66 is a leaf spring. Numerous combinations of springs may be utilized to facilitate movement of the actuator 26 along the first channel 24.

Still referring to FIGS. 8A-8B, the extension spring 64 is connected at a proximal end 76 of the first channel 24 within the handle 12. The extension spring 64 may be attached via a screw or other connector. The free end of the extension spring 64 is connected to the actuator 26. The actuator 26 extends through the first channel 24 over a receptacle 78 in the handle 12, which extends from and is connected to the first channel 24. The flat spring 66 is attached to the receptacle 78 via a screw or other connector. As shown in the depicted embodiment, both the extension spring 64 and the flat spring 66 extend longitudinally along the x-axis.

In one embodiment for assembling the device 10, the proximal end 36 of the actuator 26 is first attached to the switch 18 and hooked onto the extension spring 64. The extension spring 64 is then looped over a post located within the first channel 24 of the handle 12. The flat spring 66 is positioned near a distal end 80 of the handle 12, under the actuator 26. The outer sheath 14 is attached to the handle 12 and the two pieces 20, 22 of the handle 12 are assembled together.

Figure 9:
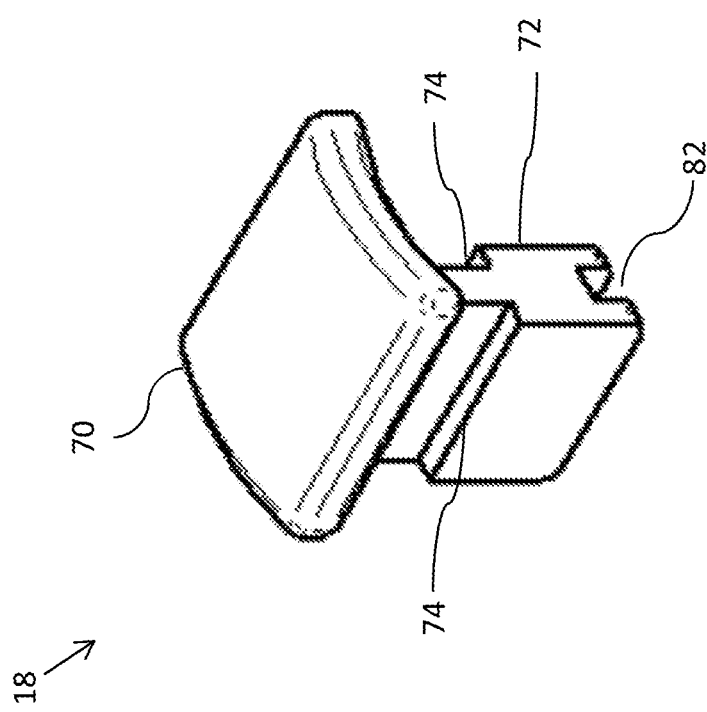
FIG. 9 is perspective view schematic representation of an illustrative embodiment of the switch of the retractable surgical cutting device of FIG. 1.

Still referring to FIGS. 8A-8B, the extension spring 64 is indirectly connected to the switch 18 via the actuator 26 to facilitate longitudinal movement of the actuator 26 along the x-axis. The switch 18 extends from the exterior of the handle 12 through a second channel 68. The second channel 68 extends from the exterior of the handle 12 into the first channel 24. An illustrative embodiment of the switch 18 is shown in FIG. 9. The switch 18 comprises an outer portion 70 connected to a body portion 72. In the depicted embodiment, the outer portion 70 has a width which is greater than the width of the second channel 68 such that the outer portion 70 of the switch 18 is maintained on the exterior of the handle 12 (as shown in FIGS. 8A-8B). Also shown in the embodiment of FIG. 9, the switch 18 has an actuator slot 82 configured for connection to the actuator 26.

Still referring to FIG. 9, the body portion 72 of the switch 18 has a pair of flanges 74. The pair of flanges 74 facilitates movement of the body portion 72 of the switch 18 along the second channel 68. In particular, the flanges 74 and the outer portion 70 of the switch 18 are dimensioned to fit around the interior of the handle 12 on either side of second channel 68 such that the outer portion 70 is above the second channel 68 and the flanges 74 are below the second channel 68 when the device 10 is in the retracted position, as shown in FIG. 8A. In the retracted position, the blade 16 is entirely within the outer sheath 14. The fit of the outer portion 70 and the flanges 74 around the handle 12 on either side of second channel 68 should be loose enough to allow the switch 18 to slide in the longitudinal direction along the x-axis to move the device 10 to the extended position.

In use, when the switch 18 is moved toward the distal end 80 of the handle 12, the extension spring 64 is extended and the switch 18 contacts the flat spring 66, as shown in FIG. 8B. The flat spring 66 forces the switch 18 upward and out through the second channel 68 until at least one of the flanges 74 contacts a shelf 84 within the second channel 68 of the handle 12. In particular, when the switch 18 is forced upward and away from the flat spring 66, at least one of the flanges 74 on the switch 18 interfaces with the shelf 84 in the handle 12 thereby locking the switch 18 in place. The shelf 84 prevents the switch 18 from disconnecting or otherwise falling out from the second channel 68 of the handle 12. When the switch 18 is locked in place against the shelf 84, the device 10 is locked in the extended position. In the extended position, the blade 16 is extended from the outer sheath 14 and exposed for use.

After use, the switch 18 is pressed downward toward the flat spring 66 and moved proximally along the second channel 68. By pressing the switch 18 downward, the flange 74 is released from the shelf 84 and the switch 18 is unlocked or free for movement proximally within the second channel 68. In one embodiment, the device 10 emits an audible indication that the switch 18 has reached the locked and/or unlocked positions. For example, the interfacing between the flange 74 and the shelf 84 may cause an audible clicking sound.

In the embodiment shown in FIGS. 8A-8B, the switch 18 is located on a top side 86 of the device 10. However, the switch 18 can be configured to be positioned at any other location on the device 10, such as the switch 18 in FIG. 10, for example. The embodiment of the switch 18 depicted in FIG. 10 also comprises an outer portion 70 connected to a body portion 72. The body portion 72 of the switch 18 has a pair of flanges 74, which facilitate movement of the body portion 72 of the switch 18 along a second channel 68, similar to the embodiment shown in FIGS. 8A-9.

Figure 10:
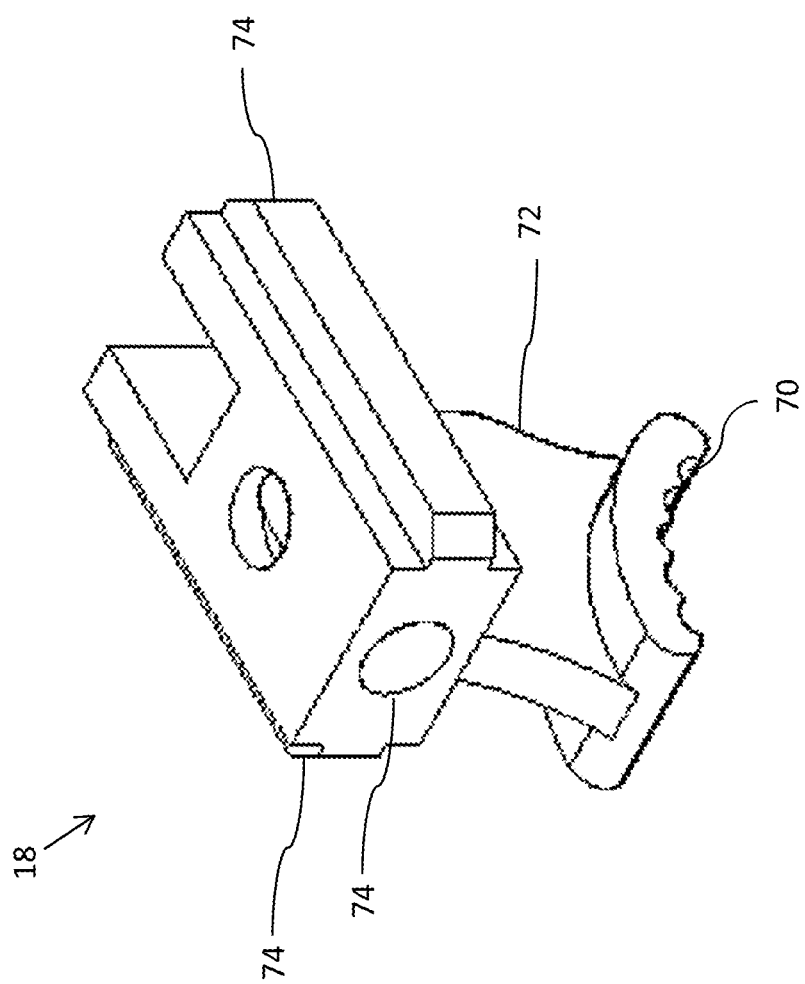
FIG. 10 is perspective view schematic representation of an alternative illustrative embodiment of the switch.
Figure 11:
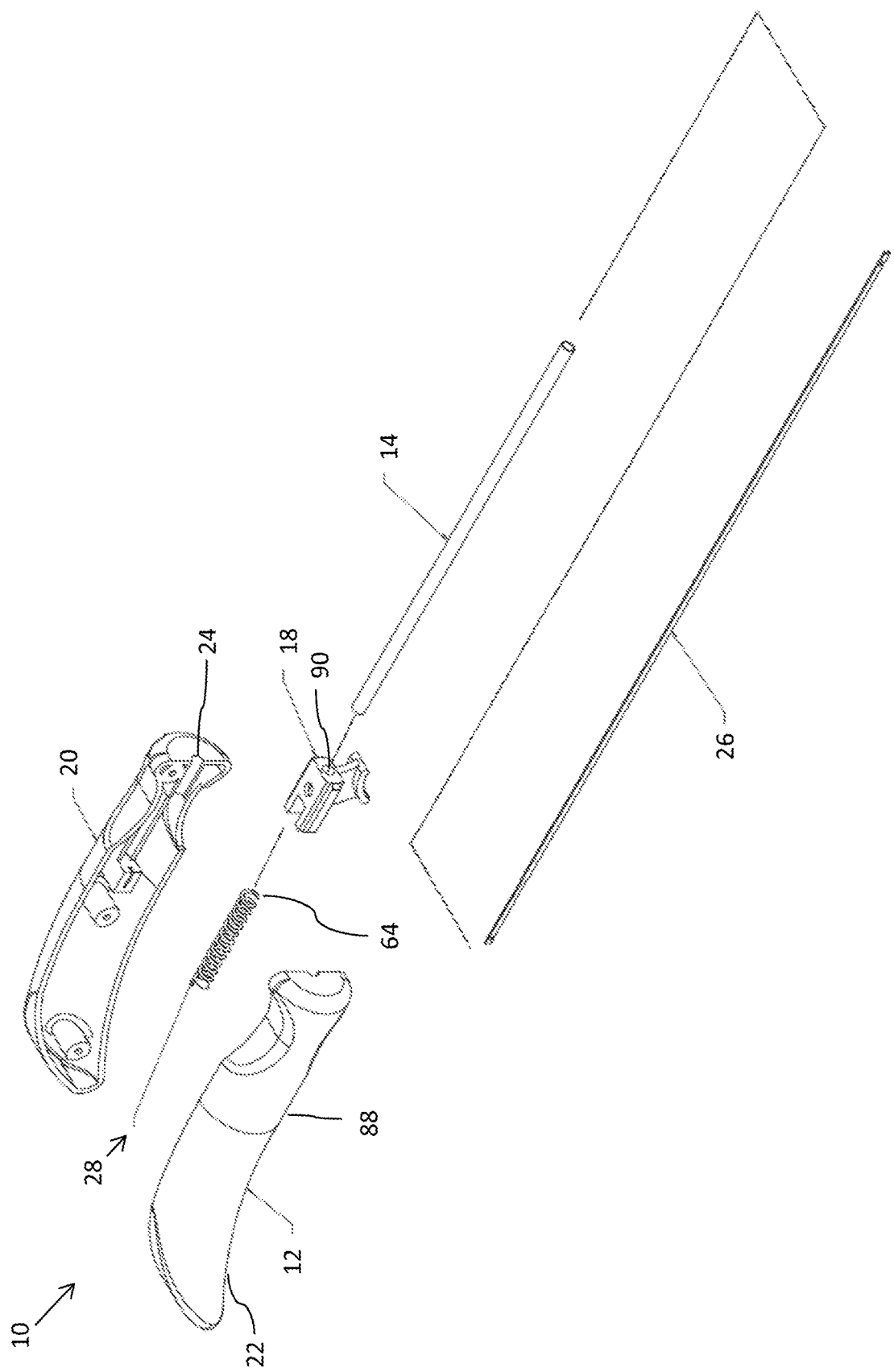
FIG. 11 is an exploded perspective view schematic representation of an alternative illustrative embodiment of the retractable surgical cutting device.

The switch 18 in FIG. 10 can be positioned on a bottom side 88 of the device 10, as shown in FIG. 11. In the embodiment depicted in FIG. 11, the switch 18 is easily accessible to the user as the switch 18 is located near the grip of the user on the handle 12 of the device 10. The first channel 24, which is connected to the actuator 26 in the embodiment shown in FIG. 2, extends through the switch 18 in the embodiment shown in FIG. 11. Specifically, the body portion 72 of the switch 18 in FIG. 10 comprises an aperture 90 for receiving and containing the actuator 26. In the depicted embodiment, the outer sheath 14 is connected to the switch 18, at the outer perimeter of aperture 90, for example.

Figure 12A:
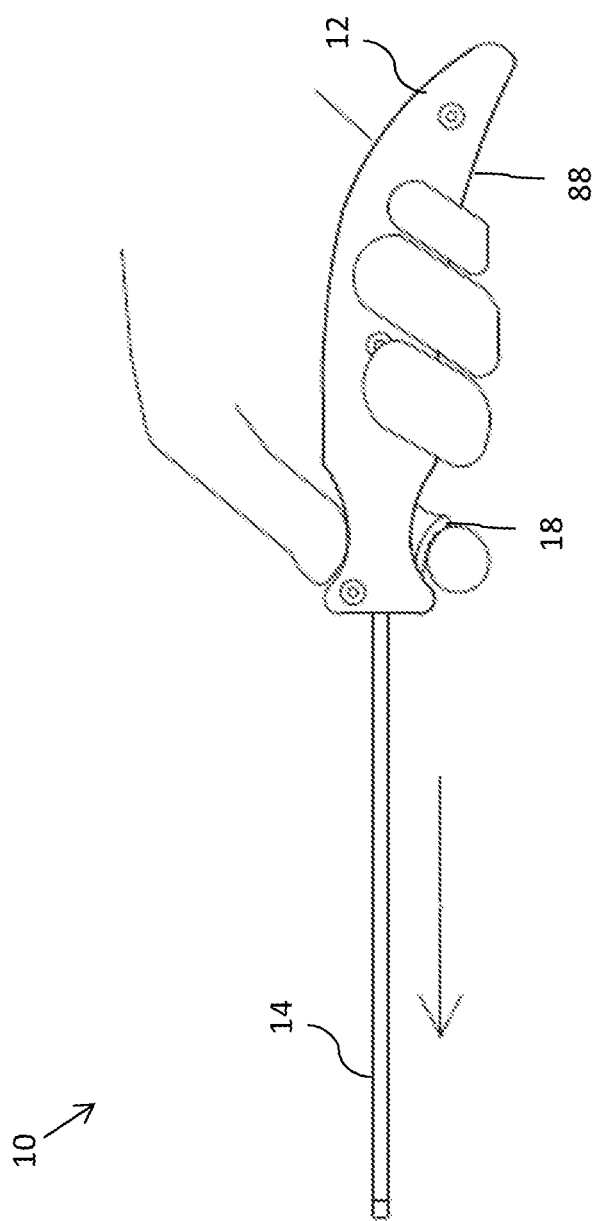
FIG. 12A is a side view schematic representation of an illustrative embodiment of the retractable surgical cutting device of FIG. 11 in the retracted position.
Figure 12B:
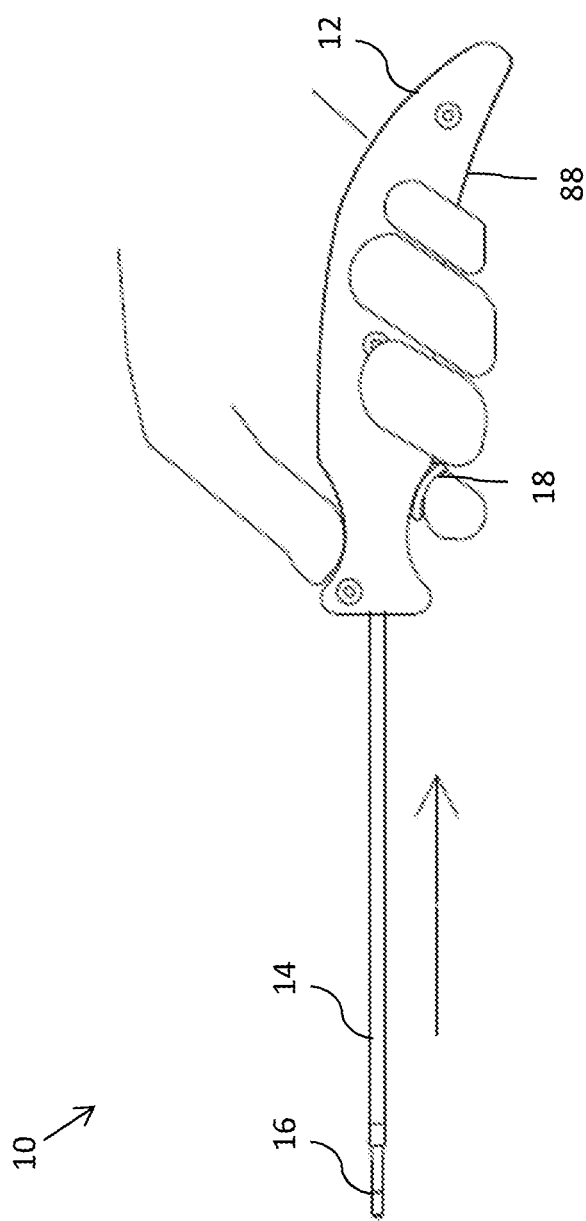
FIG. 12B is a side view schematic representation of an illustrative embodiment of the retractable surgical cutting device of FIG. 11 in the extended position.

Referring now to FIG. 12A, there is shown a side view of an illustrative embodiment of the device in FIG. 11 in the retracted position. In the retracted position, the blade 16 is contained within the outer sheath 14 and the switch 18 is not actuated. From the retracted position, pressing (i.e., actuating) the switch 18 moves the switch 18 proximally within the handle 12. As the switch 18 moves, the switch 18 pulls the connected outer sheath 14 proximally while the actuator 26 remains stationary. Proximal movement of the outer sheath 14 exposes the blade 16 at the distal end 30 of the actuator 26 for use, as shown in FIG. 12B.

Figure 13:
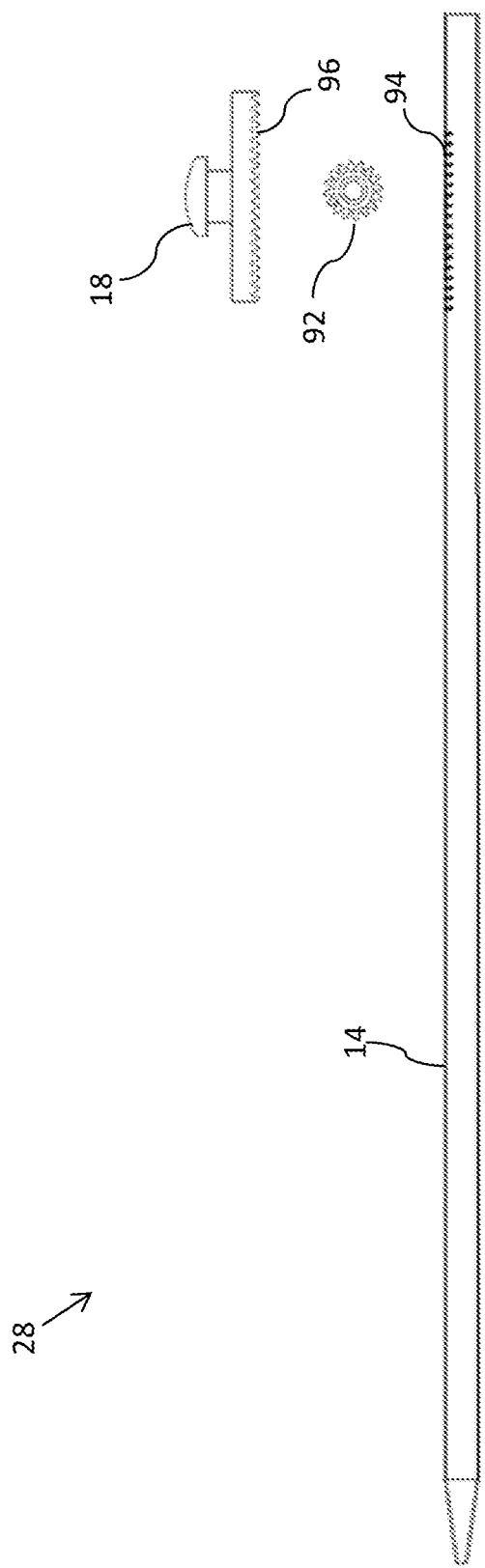
FIG. 13 is an exploded side view schematic representation of an alternative illustrative embodiment of the drive mechanism.
Figure 14:
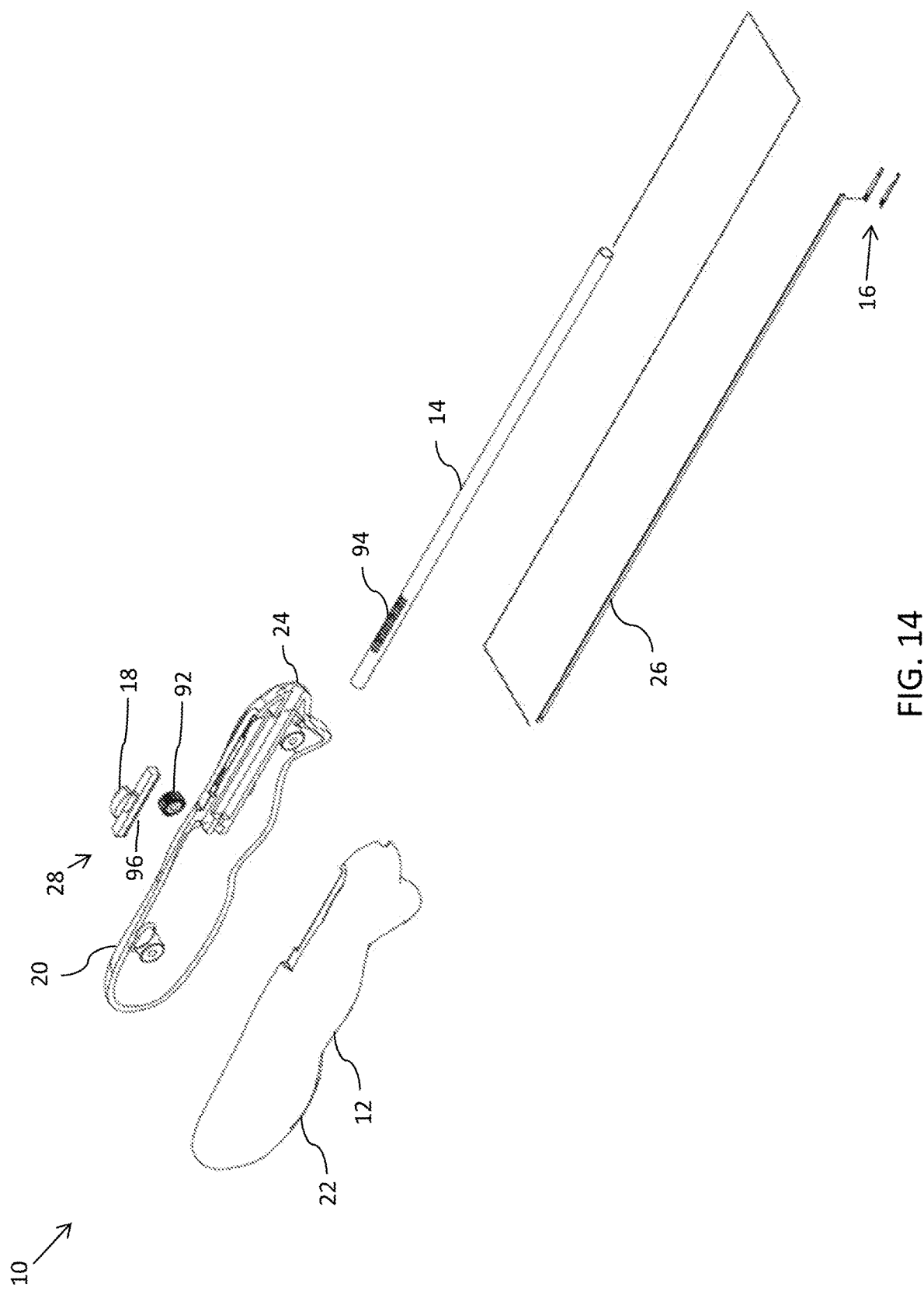
FIG. 14 is an exploded perspective view schematic representation of an illustrative embodiment of the retractable surgical cutting device with the drive mechanism of FIG. 13.
Figure 15:
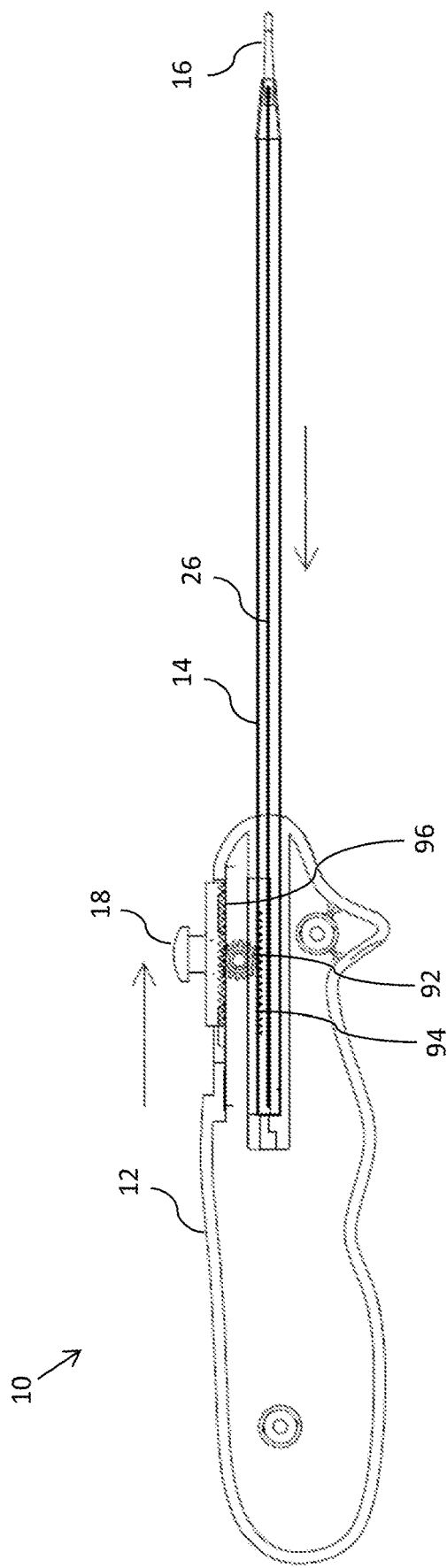
FIG. 15 is a side view schematic representation of an illustrative embodiment of the retractable surgical cutting device of FIG. 14 in the extended position.

Referring now to FIGS. 13-15, there are shown various views of an alternative embodiment for the drive mechanism 28. In the embodiment depicted in FIG. 14, the drive mechanism 28 is a rack and pinion assembly comprising the switch 18, a gear 92, and a rack 94 (or treads) on the outer sheath 14. As shown in FIG. 14, the outer sheath 14 extends through the first channel 24. The rack 94 on the outer sheath 14 interfaces with the gear 92 within the handle 12, which also interfaces with a bottom side 96 of the switch 18. The bottom side 96 of the switch 18 also comprises a rack (or treads), which engages the gear 92. From a retracted position, the switch 18 is moved distally, which causes the bottom side 96 of the switch 18 to rotate the gear 92. Rotation of the gear 92 pulls the outer sheath 14 proximally by the rack 94. As the outer sheath 14 moves proximally into the handle 12, the actuator 26 remains stationary causing exposure of at least a portion of the blade 16, as shown in FIG. 15. According to another embodiment, a locking mechanism is provided which can be actuated by a user to selectively stop the ability of the gear 92 to rotate over the rack 94 (and be reversed/released to allow rotation of the gear 92 over the rack 94). Such a locking mechanism can include a push button, a lever arm, detent or other mechanism, for example, which blocks the gear 92 from rotating over the rack 94 (as should be understood by a person of ordinary skill in the art in conjunction with a review of this disclosure).

Figure 16A:
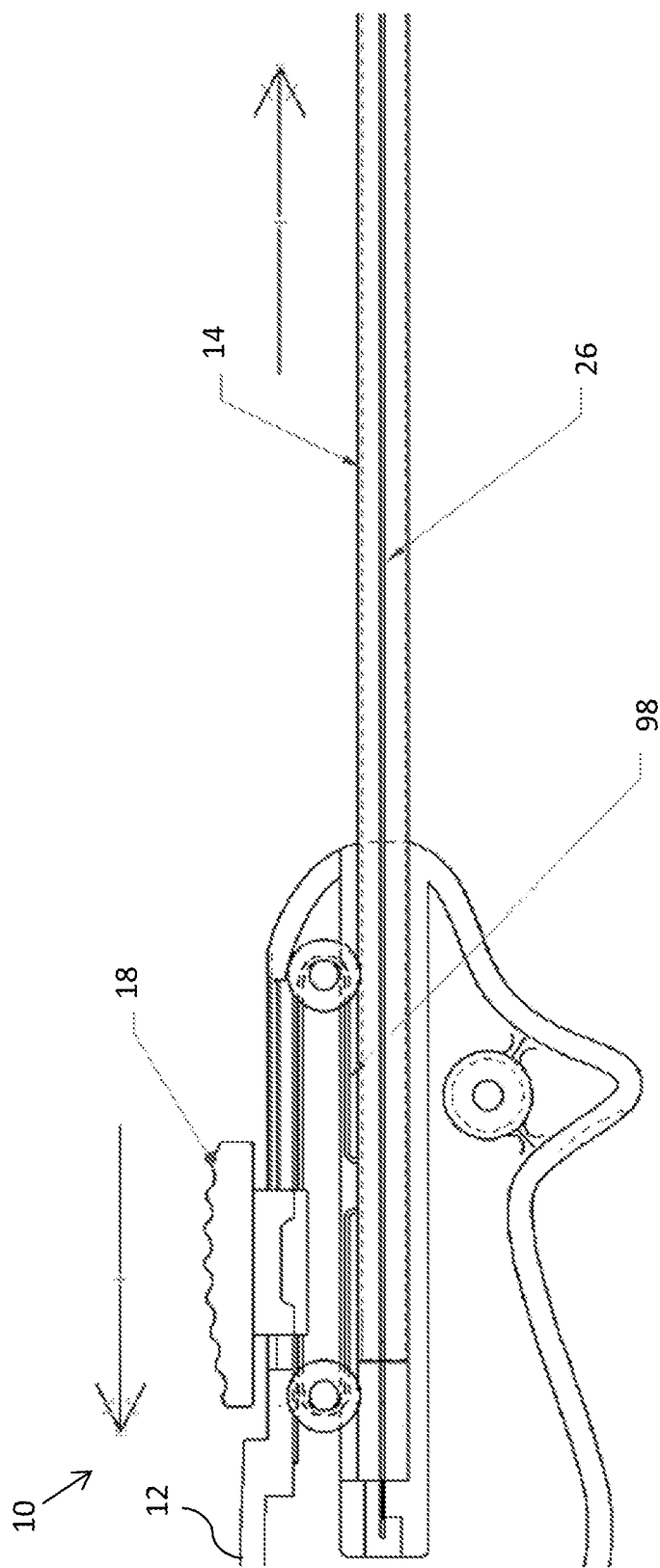
FIG. 16A is a side view schematic representation of an alternative illustrative embodiment of the drive mechanism of the retractable surgical cutting device in the retracted position.
Figure 16B:
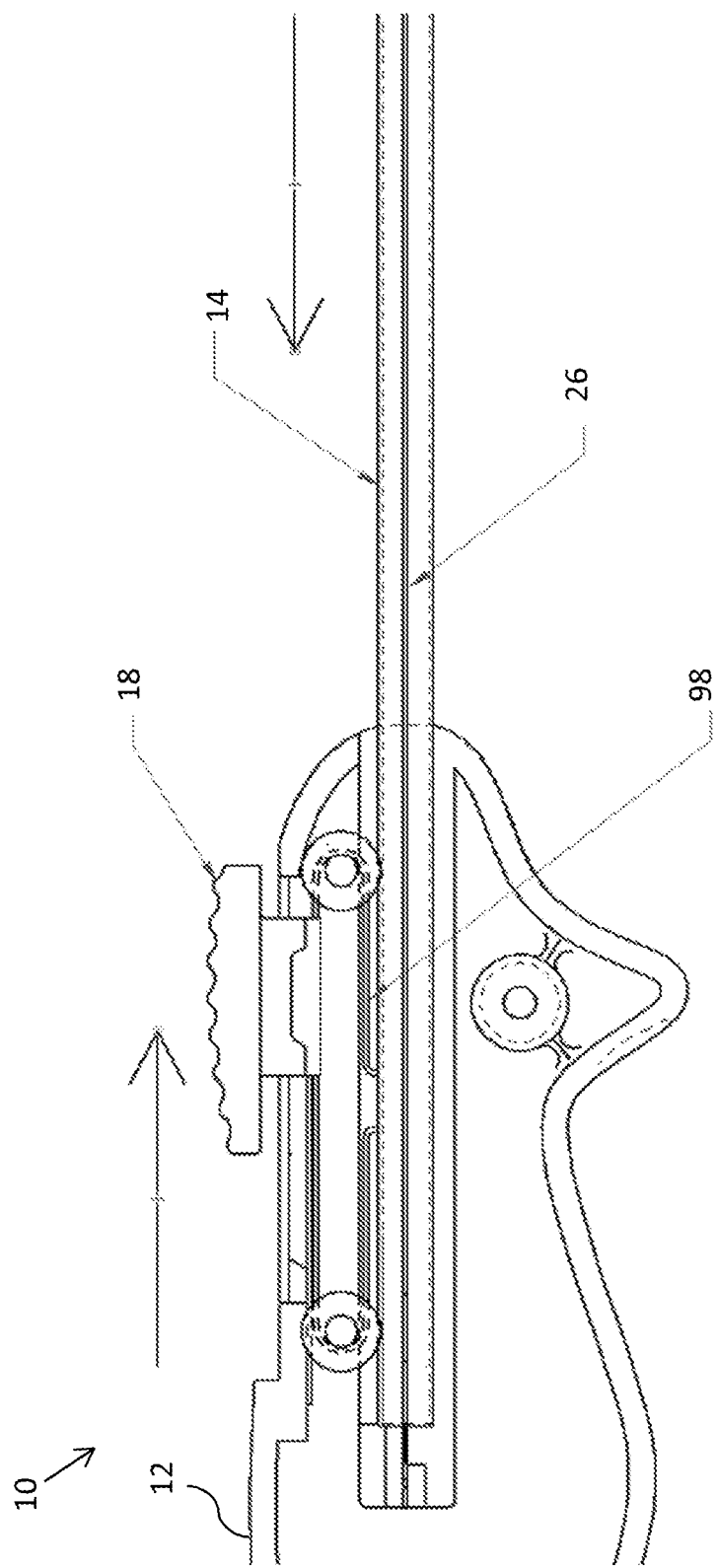
FIG. 16B is a side view schematic representation of an illustrative embodiment of the drive mechanism of the retractable surgical cutting device of FIG. 16A in the extended position.

In another embodiment, shown in FIGS. 16A-16B, the drive mechanism 28 is a sliding wire assembly. The sliding wire assembly comprises the switch 18, a wire (or flat stock) 98, and the outer sheath 14. In the depicted embodiment, the wire 98 is attached to both the switch 18 and the outer sheath 14, and is loosely contained by screws, a molded channel, or other known connectors. FIG. 16A shows the device 10 comprising the sliding wire assembly in the retracted position. As the switch 18 is moved distally toward the distal end 30 of the actuator 26 (as shown in FIG. 16B), the wire 98 moves around the screws or within the molded channels, which in turn moves the outer sheath 14 proximally in a direction opposing the direction of movement of the wire 98 and the switch 18. As the outer sheath 14 moves proximally, the actuator 26 remains stationary and the blade 16 is exposed for use. In one embodiment, the wire or flat stock 98 is composed of stainless steel. However, any other suitable compositions may be used.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A retractable surgical cutting device, comprising:
a handle having a first channel extending therethrough;
a switch located on the handle which is movable between a retracted position and an extended position;
an actuator which extends through the first channel and connects to a proximal end of the first channel within the handle;
a blade at a distal end of the actuator;
an outer sheath connected to the handle and surrounding the actuator and at least a portion of the blade;
wherein the outer sheath interfaces with the switch;
a drive mechanism connected to the switch within the handle such that when the switch moves from the retracted position to the extended position, the outer sheath is configured to move from an extended position to a retracted position while the blade remains stationary; and
wherein when the outer sheath is in the extended position, the blade is positioned within the outer sheath and when the outer sheath is in the retracted position, at least a portion of the blade is positioned outside of the outer sheath.

2. The device of claim 1, wherein the drive mechanism comprises an extension spring attached at the proximal end of the first channel and connected to the switch.

3. The device of claim 2, further comprising an aperture extending through the switch, the aperture configured to contain the actuator, wherein the outer sheath is attached to the switch.

4. The device of claim 1, wherein the drive mechanism comprises a first rack extending along a portion of an exterior surface of the switch facing the outer sheath and a second rack extending along a portion of an exterior surface of the outer sheath facing the first rack, with a gear interfacing therebetween.

5. The device of claim 1, wherein the drive mechanism comprises a wire looped around a connector, the wire connected to both the switch and the outer sheath.

6. The device of claim 1, wherein the drive mechanism comprises a wire looped around a molded channel in the handle, the wire connected to both the switch and the outer sheath.

7. The device of claim 1, wherein the blade and the actuator are formed of two separate structures.

8. The device of claim 7, wherein the actuator comprises a first notch and a second notch and the blade comprises an aperture such that first notch engages the blade on a first side of the aperture and the second notch engages the blade on a second side of the aperture, the second side substantially opposing the first side.

9. A method for cutting tissue, comprising the steps of:
providing a retractable surgical cutting device having a handle with a first channel extending therethrough, a switch located on the handle which is movable between a retracted position and an extended position, an actuator which extends to a proximal end of the first channel, a blade at a distal end of the actuator, an outer sheath interfacing the switch, the outer sheath surrounding the actuator; and a drive mechanism connected to the switch within the handle;
moving the switch in a first direction from a retracted position to an extended position along a longitudinal x-axis extending through the device;
moving the outer sheath, via the drive mechanism, relative to the actuator from an extended position to a retracted position; and
exposing at least a portion of the blade while the blade remains stationary.

10. The device of claim 9, further comprising the steps of:
moving the switch in a second direction, opposing the first direction, along the longitudinal x-axis extending through the device;
moving the outer sheath, via the drive mechanism, relative to the actuator; and
retracting the blade within the outer sheath.

* * * * *